(12) United States Patent
Dine

(10) Patent No.: US 11,517,388 B2
(45) Date of Patent: *Dec. 6, 2022

(54) POCKET AND DRAPE SYSTEM FOR PROVIDING STERILE FIELDS

(71) Applicant: O&M Halyard, Inc., Mechanicsville, VA (US)

(72) Inventor: Ann Dine, Sherrills Ford, NC (US)

(73) Assignee: O&M Halyard, Inc., Mechanicsville, VA (US)

( * ) Notice: Subject to any disclaimer, the term of this patent is extended or adjusted under 35 U.S.C. 154(b) by 72 days.

This patent is subject to a terminal disclaimer.

(21) Appl. No.: 16/935,257

(22) Filed: Jul. 22, 2020

(65) Prior Publication Data

US 2020/0345443 A1 Nov. 5, 2020

Related U.S. Application Data

(63) Continuation of application No. 16/047,440, filed on Jul. 27, 2018, now Pat. No. 10,758,312.

(60) Provisional application No. 62/539,860, filed on Aug. 1, 2017.

(51) Int. Cl.

| A61B 46/10 | (2016.01) |
|---|---|
| A61B 50/30 | (2016.01) |
| A61B 46/00 | (2016.01) |
| A61B 46/23 | (2016.01) |

(52) U.S. Cl.
CPC .............. *A61B 50/30* (2016.02); *A61B 46/00* (2016.02); *A61B 46/10* (2016.02); *A61B 46/23* (2016.02); *A61B 46/30* (2016.02); *A61B 46/40* (2016.02); *A61B 2050/3008* (2016.02); *A61B 2050/3015* (2016.02); *A61B 2050/318* (2016.02)

(58) Field of Classification Search
CPC ......... A61B 46/10; A61B 46/00; A61B 46/23; A61B 46/30; A61B 46/40; A61B 50/30
USPC ........................................ 206/455, 570, 776
See application file for complete search history.

(56) References Cited

U.S. PATENT DOCUMENTS

| 4,476,860 A | 10/1984 | Collins et al. |
| 4,937,299 A | 6/1990 | Ewen et al. |
| 5,010,899 A | 4/1991 | Thompson |
| 5,170,804 A | 12/1992 | Glassman |
| 5,218,071 A | 6/1993 | Tsutsui et al. |
| 5,272,236 A | 12/1993 | Lai et al. |
| 5,278,272 A | 1/1994 | Lai et al. |
| 5,322,728 A | 6/1994 | Davey et al. |

(Continued)

FOREIGN PATENT DOCUMENTS

| CN | 202960791 U | 6/2013 |
| WO | WO 2018/194841 A1 | 10/2018 |

*Primary Examiner* — King M Chu
(74) *Attorney, Agent, or Firm* — Dority & Manning, P.A.

(57) ABSTRACT

A pocket and drape system which provides one or more sterile fields, as well as the methodology for employing said pocket and drape system is provided. The pocket and drape includes a base drape material having an upper edge, a lower edge, a first side edge, and a second side edge to define a perimeter, where the base drape material also includes an inner surface and an outer surface. A first row of pockets and a second row of pockets are configured on the inner surface of the base drape material. In addition, a flap covers a portion of the inner surface of the base drape material, where the flap has a first surface and an opposing second surface, wherein the flap maintains at least one sterile field.

16 Claims, 4 Drawing Sheets

(56) References Cited

U.S. PATENT DOCUMENTS

| | | | |
|---|---|---|---|
| 5,472,775 A | 12/1995 | Obijeski et al. | |
| 5,539,056 A | 7/1996 | Yang et al. | |
| 5,571,619 A | 11/1996 | McAlpin et al. | |
| 5,596,052 A | 1/1997 | Resconi et al. | |
| 5,778,889 A | 7/1998 | Jascomb | |
| 6,090,325 A | 7/2000 | Wheat et al. | |
| 6,436,085 B1 | 8/2002 | Lauer | |
| 6,500,563 B1 | 12/2002 | Datta et al. | |
| 6,644,317 B1* | 11/2003 | Lawton | A61B 46/23 128/849 |
| 8,371,448 B1 | 2/2013 | Reaux | |
| 8,459,265 B2* | 6/2013 | Young | A61B 50/15 128/853 |
| 10,537,707 B2 | 1/2020 | Brooks et al. | |
| 2012/0267272 A1* | 10/2012 | Agrawal | A61B 50/30 206/439 |
| 2013/0075457 A1* | 3/2013 | Sato | B42F 7/08 229/67.2 |
| 2013/0152946 A1* | 6/2013 | Sosnowski | A61B 46/23 128/852 |
| 2013/0193019 A1 | 8/2013 | Gluck | |
| 2013/0240399 A1* | 9/2013 | Czajka, Jr. | B65B 25/141 206/459.1 |
| 2015/0101616 A1* | 4/2015 | Wiley | A61B 50/20 128/852 |
| 2017/0368302 A1 | 12/2017 | Brooks et al. | |
| 2019/0038372 A1 | 2/2019 | Dine | |

* cited by examiner

POCKET AND DRAPE SYSTEM FOR PROVIDING STERILE FIELDS

RELATED APPLICATIONS

The present application is a continuation of U.S. patent application Ser. No. 16/047,440, filed on Jul. 27, 2018, which claims priority to U.S. Provisional Application Ser. No. 62/539,860, filed on Aug. 1, 2017, the contents of which are incorporated herein in their entirety by reference thereto.

FIELD OF THE INVENTION

The present invention relates to sterile compartmentalized packaging. The present invention further relates to sterile compartmentalized packaging containing supplies for use in medical procedures. The present invention further relates to any procedure with multiple steps required in a sterile field in order to minimize infections, bacterial or other.

BACKGROUND OF THE INVENTION

It is well known that medical procedures require sterile supplies and/or instruments in order to avoid infections. Every year an estimated 650,000 people in the United States develop infections during a hospital stay and about 75,000 die, according to the Centers for Disease Control and Prevention (CDC). More specifically, more than 8,000 patients are killed by MRSA (methicillin-resistant *Staphylococcus aureus*). Still another bacteria, C. diff (*Clostridium difficile*), kills approximately 27,000 patients in the U.S. annually while causing sickness in about 290,000 patients. These are but two of the many infectious diseases waiting to strike down patients in U.S. hospitals today. But treatment is often provided outside of hospitals, so there exists a need to provide a sterile environment in any place where various medical procedures are conducted such as clinics, ambulances, on the street, at home, and even on the battlefield.

Care providers often use individually packaged medical supply kits that include all the medical supplies necessary for a medical procedure bundled in a single package. Many medical procedures are staged procedures, wherein some medical items or supplies in a sterile condition are required at one time period during the medical procedure and other additional medical items in a sterile condition are required at a future time period, such as minutes, hours, or days later. In these situations, use of individually packaged medical supplies is not desirable and, once opened, kits and/or trays containing the required medical supplies once that are needed during a first time period suffer the fate of having the items required in future time periods become exposed to the environment and pose a health risk when used in the future for lack of sterility.

Typically, suppliers have placed components in a kit according to specific guidelines, stacked in order of use from top to bottom. During shipping, however, these odd sized components can shift inside the kit making the stack awkward and challenging to determine the correct order of the components. Therefore, there is also a need for products and procedures for organizing the components used in staged protocol in the correct order, sequencing them to make it easier for users to follow a step by step process, and maintaining a sterile environment near the incision site, wound, or person.

SUMMARY OF THE INVENTION

The present invention relates to a sterile compartmented packaging and procedures for using same. In particular, the present invention encompasses a system, kit, or packaging system that keeps medical supplies and/or instruments used in a multi-step sequential procedure sterile so that the necessary medical supplies and/or instruments for a given stage can be accessed in stages as needed without sacrificing the sterility of the medical supplies and/or instruments. The present invention encompasses at least one sterile (e.g., such as at least two sterile fields) in a single use pocket and drape system kit.

The present invention provides a drape with two or more rows of clear or transparent pockets and a flap which maintains a second sterile field intended to hold medical components in order of use according to hospital procedural protocol in a two (or multi) part procedure. The flap can separate the base drape material into two distinct sterile fields (e.g., a first sterile field associated with a first row of pockets containing various medical supplies and/or instruments and a second sterile field associated with a second row of pockets containing various medical supplies and/or instruments). In addition, it is to be understood that the present invention also contemplates two or more flaps to separate the base drape material into three or more sterile fields (e.g., a first sterile field associated with a first row of pockets containing various medical supplies and/or instruments, a second sterile field associated with a second row of pockets containing various medical supplies and/or instruments, and a third sterile field associated with a third row of pockets containing various medical supplies and/or instruments, etc.). Further, different colored wraps may be used for different procedures for ease of convenience in a hurried setting.

In one particular embodiment, the present invention is directed to a pocket and drape system that includes a base drape material having an upper edge, a lower edge, a first side edge, and a second side edge to define a perimeter, where the base drape material has an inner surface and an outer surface; a first row of pockets configured on the inner surface of the base drape material; a second row of pockets configured on the inner surface of the base drape material; and a flap covering a portion of the inner surface of the base drape material, where the flap has a first surface and an opposing second surface, wherein the flap maintains at least one sterile field.

In another embodiment, the first row of pockets and the second row of pockets can be formed from a clear material.

In still another embodiment, a plurality of vertical seals can be present in the first row of pockets and the second row of pockets to define individual pockets in each of the first row of pockets and the second row of pockets.

In yet another embodiment, the first row of pockets and the second row of pockets can each include a free end and a sealed end. Further, a sealed end of the flap can be sealed to the sealed end of the first row of pockets or can be sealed or attached to the base drape material adjacent the sealed end of the first row of pockets. In addition, the flap can include a free end, and the flap can be movable such that the flap covers at least a portion of the second row of pockets in a first position and covers at least a portion of the first row of pockets in a second position.

In one more embodiment, a boundary can exists between the perimeter of the base drape material and the first row of pockets, the second row of pockets, or both. For instance, the boundary can span a distance ranging from about 40 millimeters to about 150 millimeters.

In an additional embodiment, the base drape material, the flap, or both can be formed from a sterilization material.

Further, the sterilization material can be a spunbond-melt-blown-spunbond (SMS) material.

In another embodiment, the first row of pockets and the second row of pockets can contain instruments, medical supplies, or a combination thereof for use in a multi-step sequential procedure. For example, the multi-step sequential procedure can be selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; laminectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

In one more embodiment, one or more elastic loops can be disposed on the base drape material.

In another particular embodiment, the present invention is directed to a method for maintaining a sterile field while performing a multi-step sequential procedure. The method includes the steps of: providing a base drape material having an upper edge, a lower edge, a first side edge, and a second side edge to define a perimeter, where the base drape material has an inner surface and an outer surface; providing a first row of pockets and a second row of pockets on the inner surface of the base drape material, where the first row of pockets and the second row of pockets contain instruments, medical supplies, or a combination thereof to be used in a multi-step sequential procedure; providing a flap covering a portion of the inner surface of the base drape material, where the flap has a first surface and an opposing second surface, where the flap covers at least a portion of the instruments, medical supplies, or a combination thereof prior to their use in the multi-step sequential procedure; and positioning the flap to cover the instruments, medical supplies, or a combination thereof not yet in use during the multi-step sequential procedure, thereby maintaining a sterile field comprising the instruments, medical supplies, or a combination thereof not yet in use during the multi-step sequential procedure.

In another embodiment, each of the first row of pockets and the second row of pockets can be formed from a clear material, where a plurality of vertical seals can be present in the first row of pockets and the second row of pockets to define individual pockets in each of the first row of pockets and the second row of pockets.

In still another embodiment, the first row of pockets and the second row of pockets can each include a free end and a sealed end, where a sealed end of the flap can be sealed to the sealed end of the first row of pockets or can be sealed or attached to the base drape material adjacent the sealed end of the first row of pockets, where the flap can further include a free end. For instance, the flap can be movable such that the flap covers at least a portion of the second row of pockets in a first position and covers at least a portion of the first row of pockets in a second position.

In yet another embodiment, a boundary can exist between the perimeter of the base drape material and the first row of pockets, the second row of pockets, or both, where the boundary can span a distance ranging from about 40 millimeters to about 150 millimeters.

In one more embodiment, the base drape material, the flap, or both can be formed from a sterilization material, where the sterilization material can be a spunbond-melt-blown-spunbond (SMS) material.

In an additional embodiment, the multi-step sequential procedure can be selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; laminectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

In one more embodiment, one or more elastic loops can be disposed on the base drape material.

The present invention ensures that users follow protocol/formulary exactly and reduces the risk of harm or spread of infection to the patient during medical care procedures.

The present invention also ensures that users follow protocol/formulary exactly and is designed to reduce the risk of harm or spread of infection during veterinary procedures.

Further, the present invention ensures that users follow protocol/formulary exactly and is designed to reduce the risk of harm or spread of infection during dental procedures.

The present invention further provides kits and procedures for use in research, lab testing, pharmaceutical testing, manufacturing, and the like.

One embodiment of the present invention encompasses IV start kits and procedures.

A further embodiment of the present invention encompasses central line dressing change kits and procedures. In addition, central line insertion and removal kits and procedures are also contemplated by the present invention.

A further embodiment of the present invention encompasses port access change kits and procedures. In addition, central line insertion and removal kits and procedures are also contemplated by the present invention.

A further embodiment of the present invention encompasses change kits and procedures for the veterinary field.

A further embodiment of the present invention encompasses change kits and procedures related to related dental care/dental procedures.

A further embodiment of the present invention encompasses change kits and procedures related to lab testing/lab procedures.

A further embodiment of the present invention encompasses change kits and procedures related to human or animal research testing.

A further embodiment of the present invention encompasses change kits and procedures related to pharmaceutical testing/manufacturing/research/delivery.

The present invention further contemplates a portable sterile field on a battlefield or other unsanitized place/area.

The present invention further contemplates kits customizable for any procedure requiring one or more sterile supplies or instruments.

Embodiments of the present invention also encompass change kits and procedures related to laceration and suture removal kits, disposable instrument kits, amenity kits, endoscopy kits, trach trays, and blood culture kits.

Embodiments of the present invention also encompass kits and procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; laminectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE FIGURES

A full and enabling disclosure of the present invention, including the best mode thereof, directed to one of ordinary skill in the art, is set forth in the specification, which makes reference to the appended figures, in which.

DEFINITIONS

Figure 1:
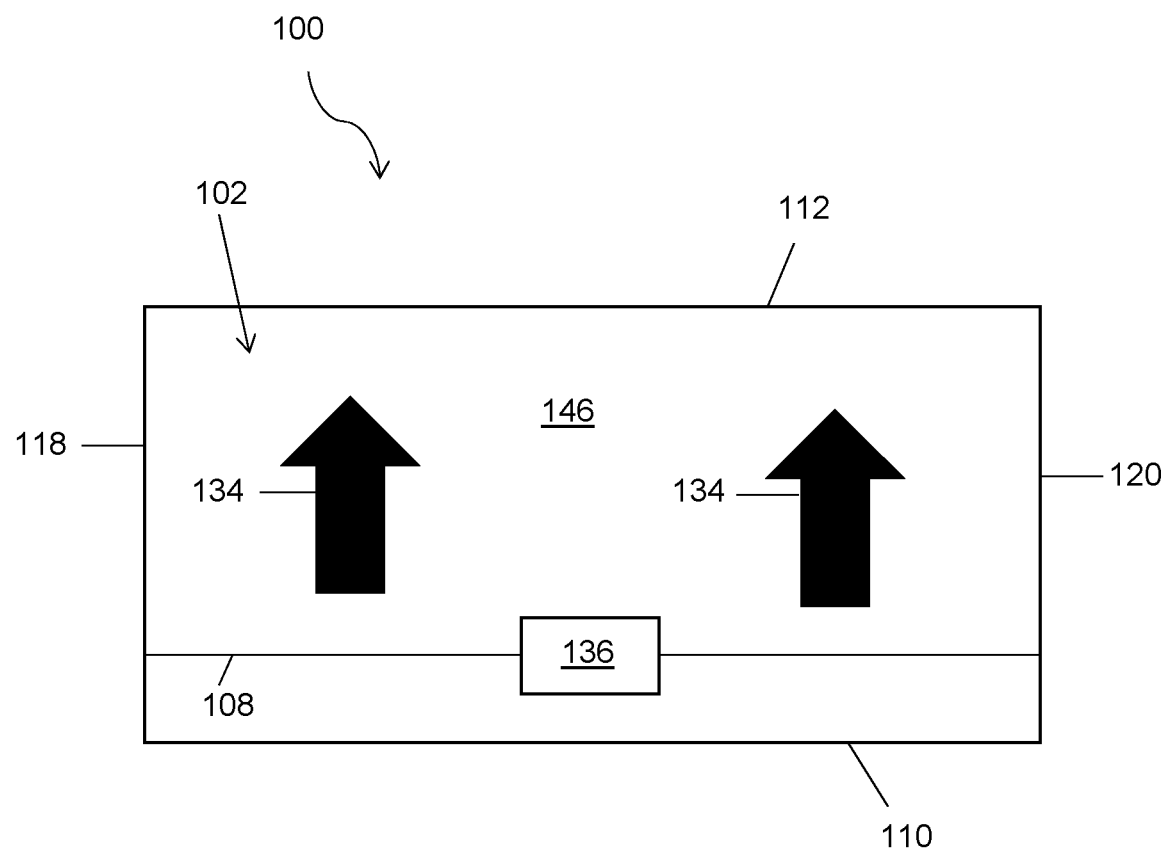
FIG. 1 illustrates one embodiment of the pocket and drape system of the present invention, where the system is ready for use after it has been folded, sealed, and sterilized.

As used herein, the term "sterilization material" refers to a flexible article composed of fabric(s) and/or flexible material(s) that is wrapped around, folded around or otherwise encloses a non-sterile article or non-sterile content prior to sterilization. Sterilization material may have multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding, and bonded carded web processes.

As used herein, the term "spunbond material" refers to a nonwoven material containing a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms.

As used herein, the term "meltblown material" refers to a nonwoven material containing fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers.

As used herein, the term "SMS laminate material" refers to fabric laminates of spunbond and meltblown materials. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 osy to 12 osy (about 3.4 gsm to about 406 gsm), or more particularly from about 0.75 to about 3 osy (about 25.4 gsm to about 101.7 gsm).

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. Before explaining the disclosed embodiments of the present invention in detail, it is to be understood that the invention is not limited in its application to the details of any particular arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

The present invention is particularly useful for medical procedures that require a sterile field. The present invention provides a drape with clear pockets and a flap which maintains a second sterile field intended to hold medical components in order of use according to hospital procedural protocol in a two (or multi) part procedure. The flap is intended to separate the drape into two sterile fields.

During a multi-part procedure that requires aseptic technique, a first row of pockets with the appropriate medical components can be used. Once the first part of the procedure is complete a flap portion of the drape can be opened up revealing a sterile field with the necessary items (e.g., in a second row of pockets) to perform the second part of the procedure.

In one particular embodiment, an exemplary kit in accordance with the present invention may include a single base drape or wrap material that includes one or more clear or transparent pockets in one or more rows, a flap to protect first set of steps associated with removal of an old wound dressing separate from second set of steps associated with application of a new dressing, and a chlorhexidine gluconate (CHG) infused material (or similar antiseptic/antimicrobial material).

Referring now to FIGS. 1-4, the various features of the pocket and drape system of the present invention will be described in more detail. Turning first to FIG. 1, one embodiment of the pocket and drape system 100 of the present invention is shown, where the pocket and drape system 100 is ready for use after it has been folded, sealed, and sterilized.

The pocket and drape system 100 includes a base drape material 102 that can be formed from a sterilization material, which can be any suitable nonwoven material. In one particular embodiment, the base drape material 102 can be in the form of a spunbond-meltblown-spunbond (SMS) laminate material. In one particular embodiment, the SMS laminate material can include a first spunbond layer and a second spunbond layer with a meltblown layer disposed therebetween. In some embodiments, the spunbond layers can be formed from a semi-crystalline polyolefin. Exemplary polyolefins may include, for instance, polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.940 g/cm$^3$; "low density polyethylene" ("LDPE") may have a density in the range of from 0.910 to 0.940 g/cm$^3$; and "high density polyethylene" ("HDPE") may have density in the range of from 0.940 to 0.960 g/cm$^3$. Densities may be measured in accordance with ASTM 1505. Particularly suitable ethylene-based polymers for use in the present invention may be available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai et al.; and U.S. Pat. No. 5,278,272 to Lai, et al., which are incorporated herein in their entirety by reference thereto for all purposes.

Of course, the spunbond layers of the SMS laminate material from which the base drape material 102 is formed are by no means limited to ethylene polymers. For instance, propylene polymers may also be suitable for use as a semi-crystalline polyolefin. Suitable propylene polymers may include, for instance, polypropylene homopolymers, as well as copolymers or terpolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments, from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. In one particular embodiment, the spunbond layers can each include a copolymer of polypropylene and polyethylene.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the polyolefins. For instance, olefin polymers may be formed using a free radical or a coordination catalyst (e.g., Ziegler-Natta or metallocene). Metallocene-catalyzed polyolefins are described, for instance, in U.S. Pat. No. 5,571,619 to McAlpin et at; U.S. Pat. No. 5,322,728 to Davey, et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes.

The melt flow index (MI) of the polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2160 grams in 10 minutes at 190° C., and may be determined in accordance with ASTM Test Method D1238-E.

The meltblown layer of the SMS laminate material can also be formed from any of the semi-crystalline polyolefins discussed above with respect to the first spunbond layer and the second spunbond layer of the laminate material. In one particular embodiment, the meltblown layer can be formed from 100% polypropylene.

Regardless of the specific polymer or polymers used to form the SMS laminate material, the SMS laminate material from which the base drape material 102 is formed can have a basis weight ranging from about 5 gsm to about 50 gsm, such as from about 10 gsm to about 40 gsm, such as from about 15 gsm to about 30 gsm.

Returning now to FIG. 1, the pocket and drape system 100 can be folded, sterilized, and sealed such that it is ready for use in any environment where a sterile field is needed, where an outer surface 146 of the base drape material 102 is exposed, such that the inner surface 144 (see FIGS. 2-4) remains sterile. A series of folds, such as in the form of a first fold line 108, a second fold line 110, and a third fold line 112, as discussed in more detail below, can be made in the base drape material 102, where the system 100 can be sealed with an attachment means 136 (e.g., a sticker, tape, adhesive, hook and loop system, etc.) at second fold line 110 in order to maintain sterility of the interior contents of the system 100 after sterilization. Further, directional indicia 134 can be disposed on the outer surface 146 of the base drape material 102 in one or more locations between a first side edge 118 and a second side edge 120 of the base drape material 102 in order to assist a user in determining the manner in which the system is to be unfolded for use.

Figure 2:
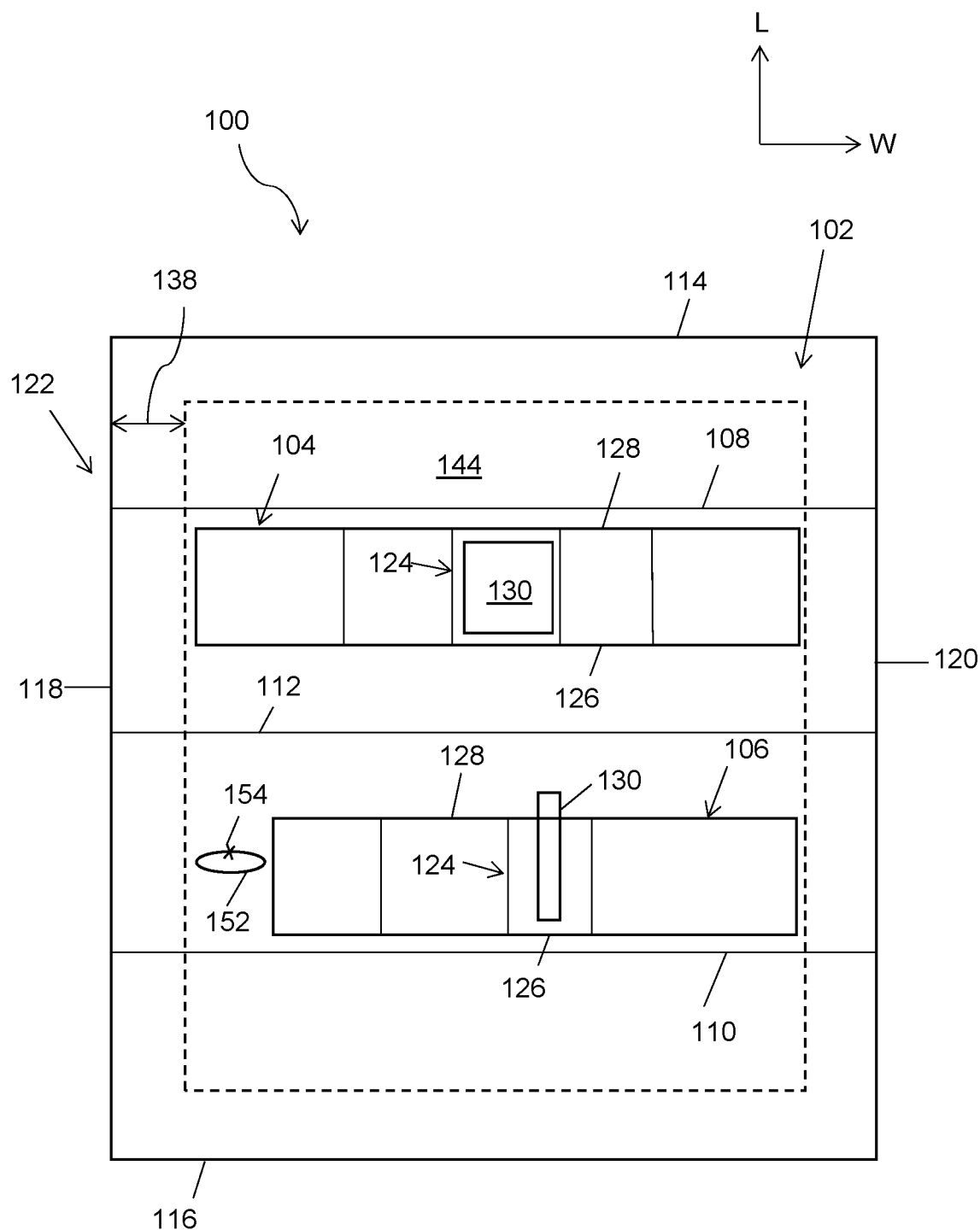
FIG. 2 illustrates the pocket and drape system of FIG. 1 after the system has been unfolded, where a flap of drape material contemplated by the present invention is not present so that the pocket components of the system are visible.

Turning now to FIG. 2, the system 100 of FIG. 1 is shown in its unfolded state, where the system can be unfolded, for example, by removing or pulling on the attachment means 136 and then unfolding the base drape material 102 at the third fold line 112, and then unfolding the base drape material 102 at the first fold line 108, followed by the second fold line 110, or by unfolding the base drape material 102 at the second fold line 110 followed by the first fold line 108. Regardless of the particular manner in which the base drape material 102 is unfolded, once unfolded, one or more flaps 132 can cover a portion of the inner surface 144 of the base drape material 102. However, a flap 132 is not shown in FIG. 2 such that the specific arrangement of other components of the system 100 can be shown in detail, and the flap 132 is discussed in more detail with respect to FIGS. 3 and 4. Specifically, FIG. 2 illustrates the arrangement of various components present on the inner surface 144 of the base drape material 102. As shown, a first row of pockets 104 and a second row of pockets 106 are disposed on the inner surface of the drape material such that a boundary 138 between the perimeter 122 of the base drape material 102 defined by upper edge 114, first side edge 118, lower edge 116, and second side edge 120 and either the first row of pockets 104 and/or the second row of pockets 106 has spans a distance in the width W direction and the length L direction of at least about 40 millimeters, such as at least about 45 millimeters, such as at least about 50 millimeters. For instance, boundary 138 between the perimeter 122 of the base drape material 102 and the first row of pockets 104 and/or the second row of pockets 106 can span a distance ranging from about 40 millimeters to about 150 millimeters, such as from about 45 millimeters to about 125 millimeters, such as from about 50 millimeters to about 100 millimeters. Without intending to be limited by any particular theory, the present inventor has found that a boundary 138 spanning such a distance can help in maintaining the sterility of the system 100.

Turning now to the first row of pockets 104 and the second row of pockets 106, the rows of pockets can include any suitable number of individual compartments of varying sizes depending on what supplies 130 are required for any given procedure for which the system 100 is being used. For illustrative purposes only, the first row of pockets 104 in FIG. 2 includes five individual pockets of different sizes, while the second row of pockets 106 includes four individual pockets of different sizes, where the individual pockets are formed via a plurality of vertical seals 124 in each row of pockets 104 and 106. As shown in FIG. 2, the first row of pockets 104 and the second row of pockets 106 each include a sealed end 126 and a free end 128, whereby supplies 130 can be inserted into the individual pockets in each row via the free or unsealed end 128. Further, it is to be understood that although only two rows of pockets are shown, any suitable number of rows of pockets can be utilized so long as a sufficient boundary 138 as described above is maintained between the perimeter 122 of the base drape material and any additional rows of pockets. Regardless of the particular number of pockets, number of rows of pockets, and size of each individual pocket, the pockets can be formed from a clear or transparent material such that a user can easily identify the various supplies 130 contained within in each pocket. Depending on the procedure for which the system is being used, the supplies 130 can include, for example, hand sanitizer, alcohol prep pads, saline ampoules, gloves, masks, bouffant caps, surgical gowns, thermometers, measuring tape, scissors, scalpels, hemostats, syringes, tape, bandages, swabs, wipes, suture kits, skin closure tape, wound closures, antibiotic applicators or wands, antibiotic creams/gels/lotions/sprays, scalpel blades, catheters, catheter securement devices, filter straws, drapes, tourniquets, room stop signs, and the like.

Further, it is to be understood that, in some embodiments, one or more elastic loops 152 can be disposed on the base drape material 102 in alignment with one or more of the rows of pockets 104 and 106. In addition, the elastic loop 152 can be secured to the base drape material 102 via any suitable attachment means 154 such as tape, adhesive, bonding, sewing, etc.). Such an elastic loops 152 can be used to securely and snugly hold certain supplies 130 in place such as instruments that may be prone to fall out of a pocket during movement or transport of the pocket and drape system 100, which can help enhance the sterility of the pocket and drape system 100, as certain instruments may have sharp tips that could potentially create holes, cuts, or pin pricks in the base drape material 102 were such instruments to fall out of a pocket.

Figure 3:
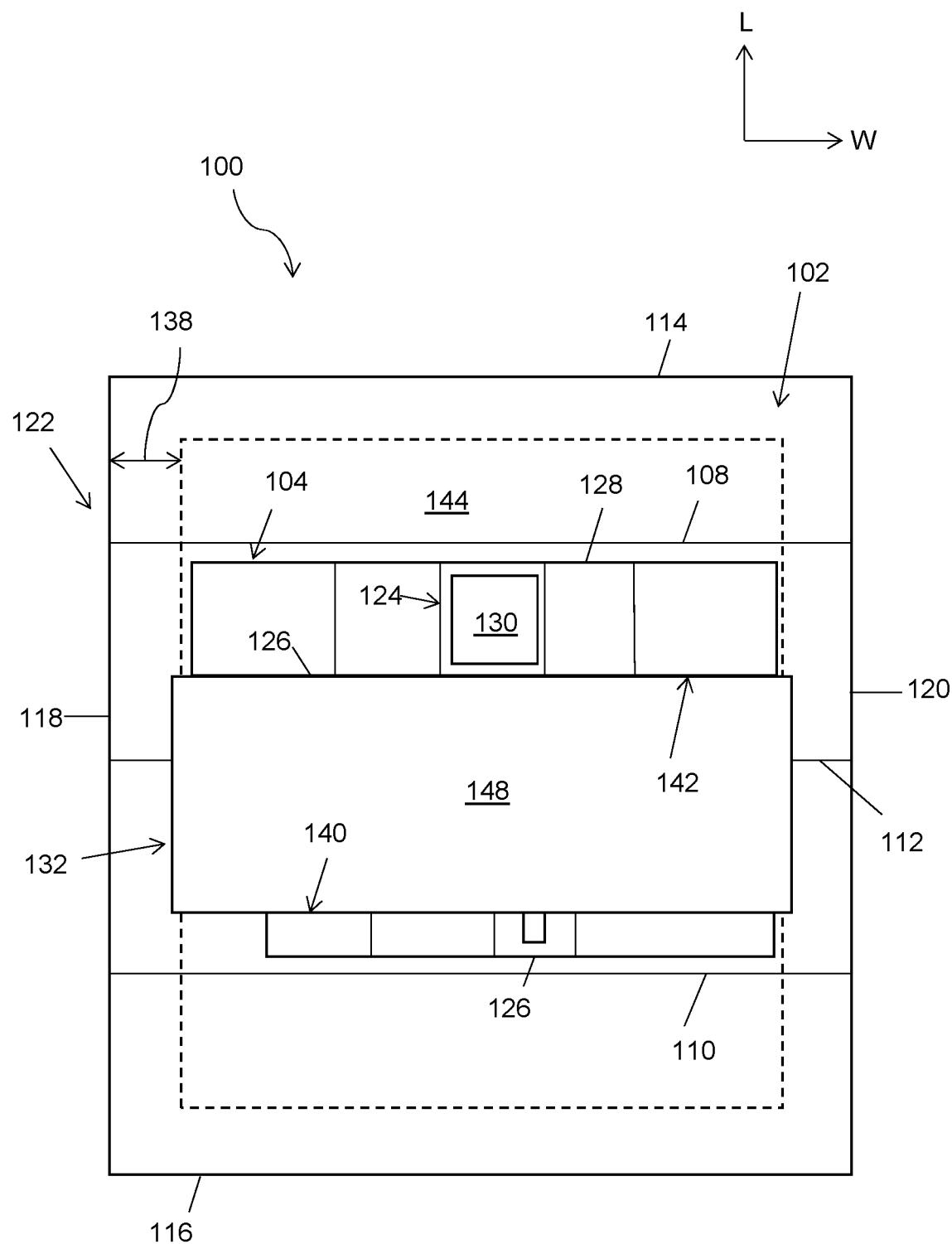
FIG. 3 illustrates the pocket and drape system of FIG. 1 after the system has been unfolded, where a flap contemplated by the present invention is illustrated in a first position.
Figure 4:
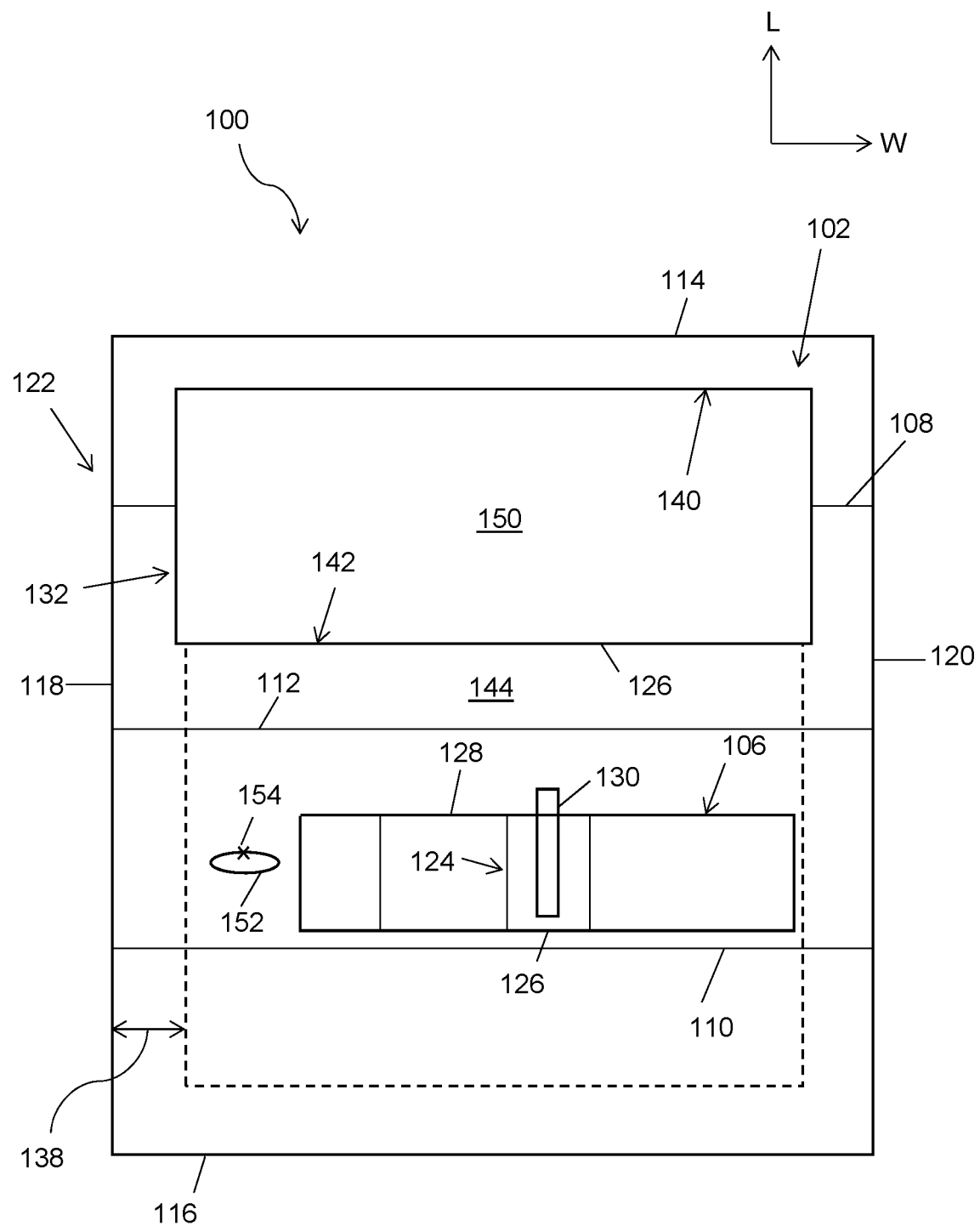
FIG. 4 illustrates the pocket and drape system of FIG. 1 after the system has been unfolded, where a flap contemplated by the present invention is illustrated in a second position.

Now that the first row of pockets 104, the second row of pockets 106, the elastic loops 153, and their contents have been described in detail, the flap 132 visible when the system 100 is first unfolded is described in references to FIGS. 3 and 4. FIG. 3 illustrates the pocket and drape system 100 after the system 100 has been unfolded, where the flap 132, which can be formed from the same material as the base drape material 102, is in a first position such that a first surface 148 is visible, while FIG. 4 illustrates the pocket and drape system 100 after the system 100 has been unfolded, where the flap 132 is in a second position such that an opposing second surface 150 is visible. Further, it is to be understood that various supplies 130 may be disposed on the flap 132, where such supplies 130 may be needed first during a medical procedure, and where such supplies 130 can be removed from the first surface 148 of the flap before accessing other supplies 130 that may be present in either the first row of pockets 104 or the second row of pockets 106. As shown in FIGS. 3 and 4, the flap 132 includes a free end 140 and a sealed end 142. The sealed end 142 is adjacent the sealed end 126 of the first row of pockets 140, while the free end 140 is unsealed and allows the flap 132 to be moveable from its first position where the first surface 148 as visible as shown in FIG. 3 to its send position in FIG. 4, where the second surface 150 is visible.

Referring to FIG. 3 in particular, the arrangement of the flap 132 at least partially over the second row of pockets 106, where the first surface 148 of the flap 132 is visible and the free end 140 of the flap 132 covers the free or unsealed end 128 of the second row of pockets 106 maintains the sterility of the supplies 130 contained within the second row of pockets 106 while the supplies 130 in the first row of pockets 104 are used first during any given procedure. Thereafter, when the supplies 130 contained within the second row of pockets 106 are needed during the procedure, the user can grasp the free end 140 of the flap 132 and bring it towards the free or unsealed end 128 of the first row of pockets 104, such that the free end 140 of the flap 132 rests in a second position near the upper edge 114 of the base drape material 102, where the second surface 150 of the flap 132 is visible. Then, the user can access supplies 130 contained in the second row of pockets 106, which have been maintained in a sterile condition since the flap 132 was disposed over at least the free end 128 of the second row of pockets 106 when the supplies 130 in the first row of pockets 104 were being used.

The construction of the pocket and drape system 100 described above can be carried out as follows. First, the base drape material 102 and the flap 132 can be cut to the appropriate size depending on the intended use of the pocket and drape system 100. Then, the clear or transparent material used to form the first row of pockets 104 and the second row of pockets 106 can be attached to the inner surface 144 of the base drape material 102 using any suitable attachment or sealing method. In one particular embodiment, the first row of pockets 104 and the second row of pockets 106 can be attached to the inner surface 144 of the base drape material 102 via heat sealing. However, other sealing methods can be used and include, but are not limited to, the use of a pressure sensitive adhesive, ultrasonic bonding, double sided tape, etc. Further, vertical seals 124 can be formed in the first row of pockets 104 and the second row of pockets 104 via any suitable method such as via heat sealing, sewing a seam, etc. Each pocket size can vary based on the specifications necessary for the intended use. Next, the flap 132 can be attached to the sealed end 126 of the first row of pockets 104 or can be attached to the inner surface 144 of the base drape material 102 adjacent the first row of pockets 104 via any suitable attachment method, such as in the manner described above, to create the seal 142 between the flap 132 and the first row of pockets 104 or base drape material 132, where the flap has a free end 140, and where the flap 132 initially covers the second row of pockets 106 as described above. For instance, the flap 132 can be aligned to specifications and heat sealed or attached to the first row of pockets 104 via any suitable means to produce a second barrier which will initially cover the second row of pockets 106 as described in detail above. In addition, it is to be understood that more than one flap 132 can be used depending on the number of rows of pockets and distinct sterile fields desired. For example, if three sterile fields are desired for three rows of pockets, the pocket and drape system of the present invention can include two flaps 132, where the flaps 132 can be heat sealed or attached to the first row of pockets and the second row of pockets 106 in the manner described with respect to a single flap 132.

In use, the pocket and drape system 100 is used to hold specific supplies 130 necessary for any number of medical or veterinary procedures, or any other procedure where a sterile environment is required. For instance, the pocket and drape system 100 can be used during port access dressing changes, dialysis dressing changes, peripherally inserted central catheter (PICC) dressing changes, central venous catheter (CVC) dressing changes, PICC insertion procedures, Foley catheter insertion procedures, peripheral IV placement procedures, laceration repair procedures, etc., where the supplies needed to carry out such procedures are contained in the pocket and drape system 100 described herein. For instance, a portion of the supplies 130 can be present in the first row of pockets 104, which are sterile upon opening. Once the supplies 130 in the first row of pockets 104 are depleted and/or no longer needed, the flap 132 can be lifted using an aseptic technique to expose the supplies 130 inserted into the second row of pockets 106 which can also be utilized in during the procedure. The flap 132 essentially creates a second sterile field in a single pocket and drape system 100.

The following examples serve to illustrate the various uses of the claimed invention in actual practice in the medical field.

Example 1—Port Access Dressing Change

The following steps can be performed when utilizing the pocket and drape system of the present invention when changing port access dressing.

1. Assess patient for CHG and/or TEGADERM™ allergy.
2. Determine if patient needs a power injectable needle.
3. Gather appropriate supplies including the pocket and drape system kit, including a correct size noncoring safety needle, correct size sterile gloves, and needleless connectors.
4. Explain procedure to patient.
5. Clean surface to be used to hold the pocket and drape system kit with germicidal wipe (e.g., overbed table).
6. Retrieve the pocket and drape system kit and remove kit from packaging on cleaned surface.
7. Don mask and place mask on patient.
8. Open pocket and drape system kit at first fold line.
9. Perform hand hygiene with antiseptic hand cleanser.
10. Don clean gloves.
11. Disconnect any infusions.
12. Scrub the needleless connector with alcohol prep pad for at least 15 seconds and allow to dry completely. If removing CUROS™ or a similar port protector, ensure it has been in place for a minimum of 1 minute.
13. Attach saline flush syringe to needleless connector maintaining sterility after removing protective cap from distal end of syringe.
14. Verify blood return.
15. Flush lumen with 10 milliliter sterile syringe using vigorous pulsatile technique to clear lumen (flush with heparin solution as prescribed if not reaccessing device). Leave 0.5 millimeter in syringe before detaching (do not bottom out syringe).
16. Remove dressing and discard.
17. Grasp needle with dominant hand while supporting the vascular access device with non-dominant hand, utilizing safety mechanism of needle.
18. Pull needle straight up and out of vascular access device and discard in sharps container.
19. Assess site for signs of infection or drainage. If not reaccessing, apply bandage over insertion site.
20. Remove and discard gloves. Set aside second set of sterile gloves and hand sanitizer gel packet.

21. Fully open kit aseptically.
22. Drop noncoring needle and sterile saline into sterile field.
23. Perform hand hygiene with antiseptic hand cleaner.
24. Don sterile gloves.
25. Activate CHG wand and cleanse skin with solution using a back and forth motion for 30 seconds. Allow CHG to completely dry.
26. Attach sterile saline syringe to needleless connector(s) and prime. Attach primed needleless connector(s) to noncoring needle and prime. Leave syringe attached.
27. Open CHG gel pad.
28. Apply sterile drape, absorbent side up, adjacent to insertion site.
29. Apply skin protectant and allow to dry. Never apply skin protectant under CHG gel pad.
30. Stabilize port with non-dominant hand and insert noncoring needle perpendicular to the skin, advancing until needle contacts port base.
31. Verify blood return.
32. Flush lumen with 10 milliliter syringe using vigorous pulsatile technique to clear lumen (flush with heparin solution as prescribed if not reaccessing device). Leave 0.5 milliliter in syringe before detaching (do not bottom out syringe).
33. Position CHG gel pad around needle.
34. Apply dressing: shirt—apply dressing to cover the insertion site; pants—apply pre-cut securement tape strip under the extension legs and over the dressing border; belt—apply dressing label with date, time, gauge, length, if powerport and initials.
35. Secure extension tubing with tape.
36. Discard supplies. Remove gloves and masks. Perform hand hygiene.
37. Document procedure in patient record. Notify charge nurse if early dressing change.

Example 2—Dialysis Dressing Change

The following steps can be performed when utilizing the pocket and drape system of the present invention when changing a dialysis dressing.
1. Assess patient for CHG and/or TEGADERM™ allergy.
2. Gather appropriate supplies including the pocket and drape system kit, including a central line dressing kit and correct size sterile gloves.
3. Explain procedure to the patient.
4. Clean surface to be used to hold the pocket and drape system kit with germicidal wipe (e.g., overbed table).
5. Retrieve the pocket and drape system kit and remove kit from packaging on cleaned surface.
6. Don mask and place mask on patient.
7. Open pocket and drape system kit at first fold line.
8. Perform hand hygiene with antiseptic hand cleanser.
9. Don clean gloves.
10. Apply drape, absorbent side up, adjacent to insertion site.
11. Measure external length of catheter from insertion site to zero mark.
12. Remove dressing by pulling towards insertion site. If needed, use alcohol prep pads to loosen dressing edges. If needed, apply tape strips to stabilize tubing. If CHG gel pad has adhered to catheter add 1-2 gtts sterile saline to gel paid, wait until absorbed. CHG should release. Repeat until CHG is no longer adherent.
13. Assess site for signs of infection or drainage.
14. Remove and discard gloves. Set aside second set of sterile gloves and hand sanitizer gel packet.
15. Open pocket and drape system at second fold line.
16. Fully open packet aseptically.
17. Perform hand hygiene with antiseptic hand cleanser.
18. Don sterile gloves.
19. Grasp catheter lumens with sterile 4×4 gauze and hold away from patient's skin.
20. Use alcohol swab sticks to remove dried blood at insertion site, if applicable, and allow to dry completely.
21. Activate CHG wand and cleanse skin with solution using a back and forth motion for 30 seconds. Allow CHG to completely dry.
22. Apply skin protectant and allow to dry. Never apply skin protectant under CHG gel pad.
23. Center CHG gel pad over insertion site before laying dressing down.
24. Apply dressing: shirt—apply dressing to cover the insertion site; pants—apply pre-cut securement tape strip under the extension legs and over the dressing border; belt—apply dressing label with date, time, and initials.
25. Discard supplies. Remove gloves and masks. Perform hand hygiene.
26. Document procedure in patient record. Notify charge nurse if early dressing change. Document external length of catheter in EHR and compare to previous measurement.

Example 3—PICC Dressing Change

The following steps can be performed when utilizing the pocket and drape system of the present invention when changing a PICC dressing.
1. Assess patient for CHG and/or TEGADERM™ allergy.
2. Gather appropriate supplies including the pocket and drape system kit, including a central line dressing kit and correct size sterile gloves.
3. Explain procedure to the patient.
4. Clean surface to be used to hold the pocket and drape system kit with germicidal wipe (e.g., overbed table).
5. Retrieve the pocket and drape system kit and remove kit from packaging on cleaned surface.
6. Don mask and place mask on patient.
7. Open pocket and drape system kit at first fold line.
8. Perform hand hygiene with antiseptic hand cleanser.
9. Don clean gloves.
10. Apply drape, absorbent side up, adjacent to insertion site.
11. Measure external length of catheter from insertion site to zero mark.
12. Remove dressing by pulling towards insertion site. If needed, use alcohol prep pads to loosen dressing edges. If needed, apply tape strips to stabilize tubing. If CHG gel pad has adhered to catheter add 1-2 gtts sterile saline to gel paid, wait until absorbed. CHG should release. Repeat until CHG is no longer adherent.
13. Remove STATLOCK™ or other stabilization device with alcohol prep pad to release adhesive. Secure catheter with tape strips if needed.
14. Assess site for signs of infection or drainage.
15. Remove and discard gloves. Set aside second set of sterile gloves and hand sanitizer gel packet.
16. Open pocket and drape system at second fold line.
17. Fully open packet aseptically.
18. Perform hand hygiene with antiseptic hand cleanser.

19. Don sterile gloves.
20. Grasp catheter lumens with sterile 4×4 gauze and hold away from patient's skin.
21. Use alcohol swab sticks to remove dried blood at insertion site, if applicable, and allow to dry completely.
22. Activate CHG wand and cleanse skin with solution using a back and forth motion for 30 seconds. Allow CHG to completely dry.
23. Open STATLOCK™ package.
24. Apply skin protectant to area larger than anchor pad of STATLOCK™ and allow to dry. Never apply skin protectant under CHG gel pad.
25. Apply STATLOCK™ device (closing wings/doors over PICC anchor sites) and adhere STATLOCK™ to patient skin ("click it before you stick it").
26. Apply dressing: shirt—apply dressing to cover the insertion site; pants—apply pre-cut securement tape strip under the extension legs and over the dressing border; belt—apply dressing label with date, time, and initials.
27. Discard supplies. Remove gloves and masks. Perform hand hygiene.
28. Document procedure in patient record. Notify charge nurse if early dressing change. Document external length of catheter in EHR and compare to previous measurement.

Example 4—CVC Dressing Change

The following steps can be performed when utilizing the pocket and drape system of the present invention when changing a CVC dressing.
1. Assess patient for CHG and/or TEGADERM™ allergy.
2. Gather appropriate supplies including the pocket and drape system kit, including a central line dressing kit and correct size sterile gloves.
3. Explain procedure to the patient.
4. Clean surface to be used to hold the pocket and drape system kit with germicidal wipe (e.g., overbed table).
5. Retrieve the pocket and drape system kit and remove kit from packaging on cleaned surface.
6. Don mask and place mask on patient.
7. Open pocket and drape system kit at first fold line.
8. Perform hand hygiene with antiseptic hand cleanser.
9. Don clean gloves.
10. Apply drape, absorbent side up, adjacent to insertion site.
11. Measure external length of catheter from insertion site to zero mark.
12. Remove dressing by pulling towards insertion site. If needed, use alcohol prep pads to loosen dressing edges. If needed, apply tape strips to stabilize tubing. If CHG gel pad has adhered to catheter add 1-2 gtts sterile saline to gel paid, wait until absorbed. CHG should release. Repeat until CHG is no longer adherent.
13. Assess site for signs of infection or drainage.
14. Remove and discard gloves. Set aside second set of sterile gloves and hand sanitizer gel packet.
15. Open pocket and drape system at second fold line.
16. Fully open packet aseptically.
17. Perform hand hygiene with antiseptic hand cleanser.
18. Don sterile gloves.
19. Grasp catheter lumens with sterile 4×4 gauze and hold away from patient's skin.
20. Use alcohol swab sticks to remove dried blood at insertion site, if applicable, and allow to dry completely.
21. Activate CHG wand and cleanse skin with solution using a back and forth motion for 30 seconds. Allow CHG to completely dry.
22. Apply skin protectant and allow to dry. Never apply skin protectant under the CHG gel pad.
23. Center CHG gel pad over insertion site before laying dressing down.
24. Apply dressing: shirt—apply dressing to cover the insertion site; pants—apply pre-cut securement tape strip under the extension legs and over the dressing border; belt—apply dressing label with date, time, and initials.
25. Discard supplies. Remove gloves and masks. Perform hand hygiene.
26. Document procedure in patient record. Notify charge nurse if early dressing change. Document external length of catheter in EHR and compare to previous measurement.

Example 5—PICC Insertion

The following steps can be performed when utilizing the pocket and drape system of the present invention to insert a PICC.
1. If performing procedure at the bedside, place a STOP sign on the patient room door.
2. Open the pocket and drape system kit.
3. Identify vein and insertion site. Apply tourniquet above the anticipated insertion site. Once the vein is selected, release tourniquet but keep it in place for insertion.
4. Utilize measuring tape to measure from the planned insertion site over to the sternal notch, then down to the third intercostal space.
5. Place the patient in a supine position, extending the arm away from the body.
6. Preflush the catheter.
7. Open and drop the catheter and any additional items onto the sterile field.
8. Reapply tourniquet and tighten to assess vein under ultrasound.
9. Don mask.
10. Scrub hands and don sterile gown and gloves.
11. Prep selected site with antiseptic solution. Allow to dry. Prep site from distal portion of arm to below the antecubital area. Prep around the entire circumference of arm.
12. Drape patient with full body drape, leaving area of intended insertion exposed through the drape fenestration.
13. Inject 2% lidocaine without epinephrine intradermal at intended insertion site using a small gauge needle (25 gauge).
14. Access desired vein with the appropriate IV Catheter needle using ultrasound.
15. Place the guide wire. Gently advance the guide wire through the needle/IV catheter into vessel. At no time should the wire be forced if resistance is met. Remove the needle/IV catheter, leaving the wire in place, with 4-5" of the wire exposed. Release the tourniquet at this point.
16. Enlarge the insertion site using the #11 scalpel blade to allow the introducer to easily pass through the skin.
17. Gently insert the dilator and peel apart introducer over the guide wire, making sure the guide wire is always visible at the proximal end of the introducer. If unable to advance the dilator/introducer together, first use the dilator to enlarge the area before the introducer is added.

18. Place the wire in the desired position under fluoroscopy. Remove and measure the wire then cut the catheter to the desired length utilizing scissors (less 3 cm).
19. Remove the dilator and guide wire. Apply the non-dominant thumb over the opening of the introducer to reduce blood spillage.
20. Insert the tip of the catheter into the introducer; gently advance approximately 8-10 inches.
21. Instruct the patient turn his/her head toward the cannulated arm and tuck chin onto clavicle; gently advance the rest of the catheter into the SVC, as determined under fluoroscopy. Encourage the patient to hold his/her breath or use the Valsalva maneuver to encourage the catheter downward into the SVC.
22. Once catheter is in the correct position, peel apart the introducer and remove introducer.
23. Remove the guide wire, if applicable. Immediately clamp the catheter to prevent ingress of air.
24. Attach the syringe containing heparinized saline. Open the clamp and pull back to assess for blood return. If positive, flush the catheter with 3-5 mL heparinized saline and close the clamp. Place the cap on the catheter.
25. Secure the catheter in place utilizing securement device. Suture the catheter in place using local anesthetic as indicated. (See suturing procedure).
26. Cleanse the site with alcohol swabs. Allow to dry.
27. Cover with a sterile dressing and wound closure strips.
28. Attach needleless connectors to the catheter lumens.
29. Utilize surgical tape to secure catheter lumens in place.
30. Have a physician/radiologist confirm the catheter tip placement. Do not use the catheter until placement has been confirmed.

TABLE 1

Location of Supplies Contained in Pocket and Drape System for PICC Insertion and Their Location

| Supplies Contained within Drape System on Top of Flap | Supplies Contained in 1st Row of Pockets | Supplies Contained in 2nd Row of Pockets |
|---|---|---|
| Room Stop Sign | Sterile Gloves | Alcohol Swab |
| Tourniquet | Scalpel | Transparent Dressing |
| Measuring Tape | IV Catheter, 20G | Wound Closures (3) |
| Fenestration Drape | Hypodermic safety needle | Surgical tape |
| Surgical Gown | Filter straw | Needleless valve end caps (2) |
| Bouffant Cap | Towel, absorbent | |
| Masks | Syringes | Catheter |
| Sterile Gloves | Lidocaine | Securement Device |
| Hand Sanitizer Gel | Saline | |
| Chloraprep | Scissors | |
| | Gauze 4 × 4 | |
| | Gauze 2 × 2 | |

Other Supplies

PICC Catheter w/ guidewire
Microintroducer
Introducer needle

Example 6—Foley Catheter Insertion

The following steps can be performed when utilizing the pocket and drape system of the present invention to insert a Foley catheter.

1. Verify Foley catheter order.
2. Review record for allergies (e.g., latex and iodine).
3. Explain procedure to patient.
4. Gather supplies including the pocket and drape system kit.
5. Wash hands.
6. Don clean gloves.
7. Ensure proper patient positioning: female—supine position with knees flexed and separated with feet flat on bed; male—supine with legs extended.
8. Cleanse the perineal area with soap and water; dry.
9. Prepare area for sterile field.
10. Open the pocket and drape system kit to the first fold line and drop drainage bag within the sterile field.
11. Drape patient with drapes supplied in the kit.
12. Don sterile gloves.
13. Saturate cotton balls with iodine solution.
14. Open packet of lubricant in the kit and lubricate catheter tip.
15. Examine drainage bag and ensure drain is closed.
16. Prepare insertion site sterilely: female—separate the labia with non-dominant hand and keep opening during entire cleaning process, with dominant hand, cleanse with iodine-soaked cotton balls, using a single downward motion, outer edges first, then the center, over the meatus itself, maintaining separation of labia; male—if the patient is uncircumcised, retract the foreskin before cleansing, hold the penis with non-dominant hand, stretching to a 60-90° C. angle, with dominant hand, cleanse with iodine-soaked cotton balls, using a circular motion, staring at the meatus and working outward, using 1 cotton ball for each circle.
17. With dominant hand, while holding the remainder of the catheter so that it does not touch anything but a sterile field, grasp the end of the catheter near the tip.
18. Insert the catheter into the urinary meatus until urine is returned.
19. Stop advancement if resistance is met and notify physician.
20. Attach the saline filled syringe to balloon port and inflate the balloon of the indwelling catheter.
21. Attach catheter to drainage bag.
22. Hang bag below bladder level.
23. Secure catheter drainage tubing to the patient's thigh with leg band and Velcro closure.
24. Remove supplies and disposed of per facility policy.
25. Change gloves and don clean gloves.
26. Clean perineal area with soap and water.
27. If male's foreskin has been retracted, replace it.
28. Cover patient to restore privacy.
29. Remove gloves and wash hands.
30. Document procedure and amount, color, and clarity of urine.

TABLE 2

Supplies Contained in Pocket and Drape System for Foley Catheter Insertion and Their Location

| Other Supplies | Supplies Contained in 1st Row of Pockets | Supplies Contained in 2nd Row of Pockets |
|---|---|---|
| Drainage bag | Clean gloves | Sterile gloves |
| | Fenestrated drape | Cotton balls |
| | Lower small sheet or chuck | Iodine packet |
| | | Catheter |
| | | Lubricant packet |
| | | Saline filled syringe |

TABLE 2-continued

Supplies Contained in Pocket and Drape System for Foley Catheter Insertion and Their Location

| Other Supplies | Supplies Contained in 1st Row of Pockets | Supplies Contained in 2nd Row of Pockets |
|---|---|---|
| | | Leg band |
| | | Clean up cloth |

Example 7—Peripheral IV Placement

The following steps can be performed when utilizing the pocket and drape system of the present invention to insert a peripheral IV.
1. Gather all the supplies and equipment needed, including the pocket and drape system kit.
2. Wash hands and don clean gloves.
3. Place tourniquet around the patient's arm to enhance site visualization
4. Prep selected site with antiseptic solution. Allow to dry.
5. Insert catheter utilizing proper technique.
6. Position the catheter.
7. Hold catheter with thumb of non-dominant hand and remove needle.
8. Attach extension tubing to the catheter hub.
9. Release tourniquet.
10. Secure catheter with securement device.
11. Cover the insertion site with a dressing.
12. Make sure the extension tubing contains a needle-less connector or attach a needle-less connector as needed.
13. Secure the extension tubing with tape.
14. Label per policy with date, time and initials.
15. Flush the catheter with regular saline solution as indicated.
16. Remove gloves and wash hands.

TABLE 3

Supplies Contained in Pocket and Drape System for Peripheral IV Placement and Their Location

| Other Supplies | First Row of Pocket and Drape System | Second Row of Pocket and Drape System |
|---|---|---|
| IV Catheter | Sterile Gloves | Sterile Gloves |
| Gauze | Tourniquet | Catheter |
| Transparent Dressing | Antiseptic | Dressing |
| Flush Syringe 10 ml | | Securement Device |
| | | Tape Roll |
| | | Extension Set with Valve Label |

Example 8—Laceration Repair

1. Don sterile mask and clean gloves and retrieve pocket and drape system kit.
2. Apply betadine or chlorhexidine gluconate (CHG) solution to the affected wound area.
3. Inject lidocaine if needed.
4. Mix saline and betadine solutions to prepare for wound cleaning, as appropriate. Utilize medicine cups for mixing.
5. Inspect wound and flush would with normal saline or a betadine/saline mixture, utilizing the large flush syringe, per hospital protocol.
6. Remove clean gloves.
7. Don sterile gloves.
8. Apply fenestrated drape to the wound.
9. Suture the wound applying the appropriate amount of sutures. Utilize needle holder, forceps and scissors to perform the suturing.
10. Remove fenestrated drape.
11. Wipe off antiseptic solution using clean gauze and saline.
12. Dress per policy, remove gloves and wash hands.

TABLE 4

Supplies Contained in Pocket and Drape System for Laceration Repair and Their Location

| Other Supplies | First Row of Pocket and Drape System | Second Row of Pocket and Drape System |
|---|---|---|
| Filter Straw | Clean Gloves | Sterile Gloves |
| Betadine Solution | Mask w/ Face Shield | Fenestrated Drape |
| Saline Solution | Lidocaine | Instrument: Needle Holder |
| | Syringes w/ Luer Lock | Instrument: Scissors |
| | Medicine Cups | Instrument: Hemostat |
| | Needle 18G × 1.5" | Instrument: Forceps |
| | Needle 25G × 0.625" | Towel |
| | Needle 27G × 1.5" | Gauze 4 × 4 |
| | Betadine or CHG Solution | Gauze 2 × 2 |
| | Large Flush Syringe | |

While the invention has been described with reference to certain exemplary embodiments thereof, those skilled in the art may make various modifications to the described embodiments of the invention without departing from the scope of the invention. The terms and descriptions used herein are set forth by way of illustration only and not meant as limitations. In particular, although the present invention has been described by way of examples, a variety of compositions and processes would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A pocket and drape system, the pocket and drape system comprising:
    a base drape material having an upper edge, a lower edge, a first side edge, and a second side edge to define a perimeter, wherein the base drape material has an inner surface and an outer surface, further wherein the base drape material includes a first fold line; and
    a first row of pockets configured on the inner surface of the base drape material, wherein maintaining the base drape material in a folded position at the first fold line facilitates the maintenance of a first sterile field,
    wherein a boundary exists between the perimeter of the base drape material and the first row of pockets, wherein the boundary spans a distance ranging from about 40 millimeters to about 150 millimeters.

2. The pocket and drape system according to claim 1, wherein the first row of pockets is formed from a clear material.

3. The pocket and drape system according to claim 1, wherein a plurality of vertical seals are present in the first row of pockets to define individual pockets in the first row of pockets.

4. The pocket and drape system according to claim 1, wherein the first row of pockets includes a free end and a sealed end.

5. The pocket and drape system according to claim 1, wherein the first fold line defines a first flap.

6. The pocket and drape system according to claim 5, wherein the first flap covers at least a portion of the first row of pockets when the base drape material is in the folded position at the first fold line.

7. The pocket and drape system according to claim 1, wherein the base drape material is formed from a sterilization material.

8. The pocket and drape system according to claim 7, wherein the sterilization material comprises a spunbond-meltblown-spunbond (SMS) material.

9. The pocket and drape system according to claim 1, wherein the first row of pockets contains instruments, medical supplies, or a combination thereof for use in a multi-step sequential procedure.

10. The pocket and drape system according to claim 9, wherein the multi-step sequential procedure is selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; laminectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

11. The pocket and drape system according to claim 1, wherein one or more elastic loops are disposed on the base drape material.

12. The pocket and drape system according to claim 1, further comprising a second row of pockets configured on the inner surface of the base drape material.

13. The pocket and drape system according to claim 12, wherein the base drape material further includes a second fold line, wherein maintaining the base drape material in a folded position at the second fold line facilitates the maintenance of a second sterile field.

14. The pocket and drape system according to claim 13, wherein the second fold line defines a second flap.

15. The pocket and drape system according to claim 14, wherein the second flap covers at least a portion of the second row of pockets when the base drape material is in the folded position at the second fold line.

16. A pocket and drape system, the pocket and drape system comprising:
   a base drape material having an upper edge, a lower edge, a first side edge, and a second side edge to define a perimeter, wherein the base drape material has an inner surface and an outer surface, further wherein the base drape material includes a first fold line and a second fold line;
   a first row of pockets configured on the inner surface of the base drape material; and
   a second row of pockets configured on the inner surface of the base drape material, wherein maintaining the base drape material in a folded position at the first fold line facilitates the maintenance of a first sterile field, wherein maintaining the base drape material in a folded position at the second fold line facilitates the maintenance of a second sterile field.

* * * * *